United States Patent
Sun et al.

(10) Patent No.: US 11,389,549 B2
(45) Date of Patent: Jul. 19, 2022

(54) DIAGNOSIS-TREATMENT INTEGRATED NANO-PROBE FOR $^{19}$F-MR/FLUORESCENCE MULTI-MODE MOLECULAR IMAGING AND DRUG-LOADING AND PREPARATION METHOD AND APPLICATION OF NANO-PROBE

(71) Applicant: Harbin Medical University, Harbin (CN)

(72) Inventors: Xilin Sun, Harbin (CN); Lina Wu, Harbin (CN); Jie Yang, Harbin (CN); Kai Wang, Harbin (CN); Lili Yang, Harbin (CN); Haoxiang Li, Harbin (CN); Yingbo Li, Harbin (CN); Xiaona Li, Harbin (CN); Shuang Liu, Harbin (CN)

(73) Assignee: Harbin Medical University, Harbin (CN)

( * ) Notice: Subject to any disclaimer, the term of this patent is extended or adjusted under 35 U.S.C. 154(b) by 0 days.

(21) Appl. No.: 16/856,432

(22) Filed: Apr. 23, 2020

(65) Prior Publication Data
US 2020/0261604 A1    Aug. 20, 2020

(30) Foreign Application Priority Data
Aug. 16, 2019 (CN) .......................... 201910756349.0

(51) Int. Cl.
*A61K 49/00* (2006.01)
*A61K 49/18* (2006.01)
*A61K 9/51* (2006.01)

(52) U.S. Cl.
CPC ........ *A61K 49/0093* (2013.01); *A61K 9/5123* (2013.01); *A61K 49/0002* (2013.01); *A61K 49/0041* (2013.01); *A61K 49/1824* (2013.01)

(58) Field of Classification Search
None
See application file for complete search history.

(56) References Cited

PUBLICATIONS

Xu et al. Folate receptor-targeted 19F MR molecular imaging and proliferation evaluation of lung cancer. 2018 J. Magn. Reson. Imaging 48: 1617-1625. Published online May 13, 2018. (Year: 2018).*

Wu et al. Local intratracheal delivery of perfluorocarbon nanoparticles to lung cancer demonstrated with magnetic resonance multimodal imaging. 2018 Theranostics 8: 563-574. Published Jan. 1, 2018. (Year: 2018).*

\* cited by examiner

*Primary Examiner* — Jennifer Lamberski (57) ABSTRACT

The present invention provides a $^{19}$F-MR/fluorescence multi-mode molecular imaging and drug loading diagnosis-treatment integrated nanoprobe, and a preparation method and an application. The nano-probe is a nanoparticle formed by coating a mixture of a surfactant containing a molecular targeting treatment drug and a fluorescent dye with a Perfluorocarbon (PFC) carrier; and by uniformly dispersing a mixed solution into water and glycerol, processing ultrasonically, removing a component which is not effectively coated, and purifying, the drug-loading nanoparticle capable of being used for 19 F-MR imaging may be prepared. The nano-probe may implement in-vivo 19F-MR molecular imaging; a carried molecular targeting treatment drug can implement targeted binding and targeted treatment; and by virtue of a characteristic that PFC in a nucleus may carry and release oxygen massively, an anaerobious microenvironment in the tumor is improved, a chemosensitization effect is achieved, and thus the diagnosis-treatment integration of the tumor is implemented finally.

7 Claims, 5 Drawing Sheets

DIAGNOSIS-TREATMENT INTEGRATED NANO-PROBE FOR $^{19}$F-MR/FLUORESCENCE MULTI-MODE MOLECULAR IMAGING AND DRUG-LOADING AND PREPARATION METHOD AND APPLICATION OF NANO-PROBE

CROSS REFERENCE TO RELATED APPLICATION

This application claims priority of Chinese Application No. CN201910756349 filed on 2019 Aug. 16 and entitled "Diagnosis-treatment integrated nano-probe for $^{19}$F-MR/fluorescence multi-mode molecular imaging and drug-loading and preparation method and application of nano-probe".

FIELD OF TECHNOLOGY

The present invention belongs to the technical field of medical diagnosis, and particularly relates to a $^{19}$F Magnetic Resonance (F-MR)/fluorescence multi-mode molecular imaging and drug loading diagnosis-treatment integrated nanoprobe for diagnosis and treatment of a lung cancer, and a preparation method and an application.

BACKGROUND

According to global cancer statistics, the lung cancer is a leading cause of cancer death among males all over the world and females in the developed countries. Additionally, there were highest prevalence and death rates in China and a highest cancer-related death rate in America in 2018. Most of lung cancer patients are diagnosed as a Non-Small Cell Lung Cancer (NSCLC) (87%), and other malignant tumors are attributed to a small cell lung cancer (SCLC). 80% of lung cancers are originated from a premalignant lesion on mucosal epithelial layers of the bronchus and alveolar airway, and then the lesion penetrates into potential parenchymatous tissues gradually. However, due to an insufficient resolution ratio of the Computed Tomography (CT), Magnetic Resonance (MR) or Positron Emission Tomography (PET)/CT(PET/CT), these tiny early lesions cannot be detected clinically. The traditional 1H Magnetic Resonance Imaging (MRI) has a shortage of being affected by respiratory movement and chemical shift artifacts of air tissues. The 19F MRI has the advantages of high sensitivity, high signal-to-noise ratio, high contrast, low background noise and the like after being optimized.

Perfluorocarbon (PFC) is a molecule having a structure similar to common organic compounds (such as alkanes), and the difference lies in that all hydrogen atoms can be substituted by fluorine. Hence, the PFC is applied to medical applications. The PFC has the characteristics of high biocompatibility, safety, no toxicity, high oxygen carrying capacity and the like, and may be used as a blood substitute. Moreover, it is insoluble to water and may be prepared into an aqueous emulsion. Particularly, the PFC may serve as a diagnostic imaging probe for biomedical applications and is used in blood pool imaging, inflammation imaging and cell tracking. It may release a drug selectively and quantitatively and deliver the drug to target cells quickly, thus serving as a drug release carrier. Additionally. The PFC has the obvious advantage of the high sensitivity of the 19 F MRI, and has long blood and tissue clearance time to provide enough time for MRI detection. In consequence, the 19 F MRI of the PFC has become a unique and noninvasive quantitative method, and is widely applied to evaluate physiological and pathological aspects of the tissues; and particularly, in the molecular imaging, it may make a diagnosis on early tiny lesions of the lung cancer. However, the PFC nanoprobe is merely a diagnostic probe and is not conspicuous for the treatment of the lung cancer.

As a third-generation Epidermal Growth Factor Receptor Tyrosine Kinase Inhibitor (EGFR-TKI), the AZD9291 has an action mechanism of binding with EGFR T790M via Cys-797 to form a covalent mode. It is a drug for late NSCLCs, can target the T790M tumor more effectively, keeps an activity of wild type EGFRs and may be used for clinical first-line treatment. Nevertheless, the AZD9291 is administered orally in routine, and its shortages lie in that the lipid solubility of the drug is high, the molecule is bound with multiple targets, the broad host range is increased and the drug therewith has increased toxicity and poor solubility and metabolic clearance rate. Furthermore, the local release rate of the drug is low, so that the maximum treatment efficacy on the tumor cannot be achieved. Additionally, the simple administration of the AZD9291 cannot implement the effect of obtaining a diagnostic result and giving symptomatic treatment at the same time.

For the purpose of improving these shortages, in recent researches, the diagnosis and treatment that are two separate processes are integrated into one nanocarrier, thus forming a diagnosis-treatment integrated nanoplatform. The nanotechnology has many advantages, for example, it has multifunctional modification, a high permeability and an Enhanced Permeation and Retention effect (EPR effect) for solid tumors, a high bioavailability, a high stability, targeting, and good sustained-release and controlled-release functions, and may serve as a drug release carrier. Hence, with the combination of the molecular imaging probe and the drug, an illness can be diagnosed accurately in real time and treated synchronously; and meanwhile, the efficacy can be monitored and the administration solution can be adjusted at any time during treatment, which is helpful to achieve the best treatment effect, and reduce the toxicity and side effect. Therefore, it is desirable to obtain a molecular nanoprobe capable of having diagnosis and treatment dual functions in the art.

SUMMARY

For the shortages of the prior art, an objective of the present invention is to provide a 19 F-MR/fluorescence multi-mode molecular imaging and drug loading diagnosis-treatment integrated nanoprobe, and a preparation method and an application.

The technical solutions of the present invention are as follows:

A 19 F-MR/fluorescence multi-mode molecular imaging and drug loading diagnosis-treatment integrated nanoprobe is a nanoparticle formed by coating a mixture of a surfactant containing a molecular targeting small-molecule treatment drug and a fluorescent dye with a PFC carrier.

In the above solutions, according to the 19 F-MR/fluorescence multi-mode molecular imaging and drug loading diagnosis-treatment integrated nanoprobe, the PFC is Perfluoro-15-Crown-5-Ether (PFCE).

The molecular targeting small-molecule treatment drug selects a third-generation EGFR-TKI AZD9291, and can target a T790M tumor more effectively.

The fluorescent dye is 2-dipalmitoyl-sn-glycero-3-phosphoethanolamine-N-(lissamine rhodamine B sulfonyl)(ammonium salt) (16:0 LissRhod PE) having a wavelength of 580 nm.

According to a preparation method of the 19 F-MR/fluorescence multi-mode molecular imaging and drug loading diagnosis-treatment integrated nanoprobe, a synthetic method of the drug-loading nanoparticle formed by the molecular targeting small-molecule treatment drug and the PFC uses a physical coating method, specifically, a combination of a self-assembled solvent evaporation method, a dialysis method and an emulsification-solvent volatilization method.

In the above method solutions, the method includes the following steps: using PFC as a carrier, and coating a mixture of a surfactant containing a molecular targeting small-molecule treatment drug and a fluorescent dye to form a nanoparticle; and uniformly mixing the nanoparticle obtained in the step (1) with glycerol and water to obtain the 19 F-MR/fluorescence multi-mode molecular imaging and drug loading diagnosis-treatment integrated nanoprobe.

The method specifically includes the following steps: I, uniformly mixing a molecular targeting small-molecule treatment drug with a surfactant and a fluorescent dye, the surfactant coating the molecular targeting small-molecule treatment drug physically because of a surface tension; and thereafter, dissolving into a volatile organic solvent, stirring for 10 min at a room temperature, evaporating the organic solvent via a rotary evaporator to dryness, then drying for 12 h in a vacuum drying oven at 37° C. and at last, dispersing into water via ultrasonic processing to obtain a mixture for later use.

II, Uniformly dispersing PFC into the mixture obtained in the step I, adding glycerol and the water dropwise, and mixing for 5 min in a high-pressure homogenizer to prepare into an emulsion containing the 19 F-MR/fluorescence multi-mode molecular imaging and drug loading diagnosis-treatment integrated nanoprobe.

III, Removing a component, which is uncoated effectively, with a dialysis manner in an environment at a pH of 7.4 and the room temperature from the emulsion obtained in the step II to obtain the 19 F-MR/fluorescence multi-mode molecular imaging and drug loading diagnosis-treatment integrated nanoprobe.

Relative to 5.5 mg of the molecular targeting small-molecule treatment drug in the step I, a dosage of the surfactant lecithin 95% (PC) is 45-50 mg.

Relative to 5.5 mg of the molecular targeting small-molecule treatment drug in the step 1, a dosage of the cholesterol is 5-6 mg.

Relative to 5.5 mg of the molecular targeting small-molecule treatment drug in the step 1, a dosage of the fluorescent dye is 0-1 mg.

Relative to 5.5 mg of the molecular targeting small-molecule treatment drug in the step I, a dosage of the volatile organic solvent is 100-300 μL.

The volatile organic solvent in the step I is chloroform or a mixed solvent of the chloroform and methanol.

The stirring in the step I is carried out away from light.

The ultrasonic processing in the step I has a frequency of 20-40 kHz, a power of 40-90 W and ultrasonic time of 5-10 min.

Further, a molar ratio of the PFC to the molecular targeting small-molecule treatment drug in the step II is (50-1000):1, preferably (70-200):1.

Relative to 5.5 mg of molecular targeting small-molecule treatment drug in the step I, a dosage of the glycerol is 0-0.5 g.

Relative to 5.5 mg of molecular targeting small-molecule treatment drug in the step I, a dosage of the water is 2-5 mL.

Or the water is ultrapure water.

An application of the 19 F-MR/fluorescence multi-mode molecular imaging and drug loading diagnosis-treatment integrated nanoprobe in preparing an imaging contrast agent for classification, diagnosis and treatment of a lung cancer.

The present invention provides a 19 F-MR/fluorescence multi-mode molecular imaging and drug loading diagnosis-treatment integrated nanoprobe. The 19 F-MR/fluorescence multi-mode molecular imaging and drug loading diagnosis-treatment integrated nanoprobe is a nanoparticle formed by coating a mixture of a surfactant containing a molecular targeting small-molecule treatment drug and a fluorescent dye with a PFC carrier. Such a 19 F-MR/fluorescence multi-mode molecular imaging and drug loading diagnosis-treatment integrated nanoprobe is a light purple emulsion liquid having a core-shell structure, a nanoscale size and an electropositive surface.

In the present invention, the PFC in the 19 F-MR/fluorescence multi-mode molecular imaging and drug loading diagnosis-treatment integrated nanoprobe may be absorbed by a tumor cell by means of a high permeability and an EPR effect of a solid tumor, may implement in-vivo 19 F-MR molecular imaging as well as accurate diagnosis of the tumor at a molecular level, has a slow degradation effect in the cell and may serve as a drug carrier.

The molecular targeting treatment drug (small-molecule) is a third-generation EGFR-TKI AZD9291. The drug has a strong hydrophobicity and is soluble to Dimethyl Sulfoxide (DMSO) and other organic solvents merely and insoluble to water, thus being instable and difficult to reach a target site in in-vivo circulation. However, with the utilization of the molecular nanoprobe of the present invention, problems of solubility of a hydrophobic drug and stability in the in-vivo circulation may be solved successfully, and the bioavailability and treatment effect of the drug are improved.

Preferably, the fluorescent dye is 2-dipalmitoyl-sn-glycero-3-phosphoethanolamine-N-(lissamine rhodamine B sulfonyl)(ammonium salt) (16:0 LissRhod PE) having a wavelength of 580 nm. The fluorescent dye coated in the nanoprobe of the present invention may implement optical imaging to observe a site of an animal model where the nanoprobe reaches. The nanoprobe provided by the present invention not only has targeting, but also has the advantages of good biocompatibility, strong stability and high drug loading capacity, etc.

Preferably, a synthetic method of the drug-loading nanoparticle formed by the molecular targeting treatment drug (small-molecule) and the PFC uses a physical coating method, specifically, a combination of a self-assembled solvent evaporation method, a dialysis method and an emulsification-solvent volatilization method; and thus, the efficient and stable combination between the targeting drug and the PFC is implemented, and functions on the two parts are not disturbed.

The present invention provides a preparation method of the above 19 F-MR/fluorescence multi-mode molecular imaging and drug loading diagnosis-treatment integrated nanoprobe, which includes the following steps:

Step (1): using PFC as a carrier, and coating a mixture of a surfactant containing a molecular targeting treatment drug (small-molecule) and a fluorescent dye to form a nanoparticle.

Uniformly mixing the nanoparticle obtained in the step (1) with glycerol and water to obtain the 19 F-MR/fluorescence multi-mode molecular imaging and drug loading diagnosis-treatment integrated nanoprobe.

The present invention prepares the 19 F-MR/fluorescence multi-mode molecular imaging and drug loading diagnosis-treatment integrated nanoprobe with the physical coating method. Because of a characteristic structure of the 19 F-MR/fluorescence multi-mode molecular imaging and drug loading diagnosis-treatment integrated nanoprobe, the nanoprobe having a high drug loading capacity and a uniform and stable particle size can only be formed by means of the physical coating method. If the nanoprobe is prepared with an emulsification method and a rotary membrane ultrasonic method like other nanoprobes, a system is not stable insufficiently, and both the drug and the fluorescent drug cannot be coated successfully to obtain the 19 F-MR % fluorescence multi-mode molecular imaging and drug loading diagnosis-treatment integrated nanoprobe of the present invention.

As a preferred technical solution of the present invention, the preparation method of the 19 F-MR/fluorescence multi-mode molecular imaging and drug loading diagnosis-treatment integrated nanoprobe specifically includes the following steps:

I. Uniformly mixing a molecular targeting treatment drug (small-molecule) with a surfactant and a fluorescent dye, the surfactant coating the molecular targeting treatment drug (small-molecule) physically because of a surface tension; and thereafter, dissolving into a volatile organic solvent, stirring for 10 min at a room temperature, evaporating the organic solvent via a rotary evaporator to dryness, then drying for 12 h in a vacuum drying oven at 37° C., and at last, dispersing into water via ultrasonic processing to obtain a mixture for later use.

II, Uniformly dispersing PFC into the mixture obtained in the step I, adding glycerol and the water dropwise, and mixing for 5 min in a high-pressure homogenizer to prepare into an emulsion containing the 19 F-MR/fluorescence multi-mode molecular imaging and drug loading diagnosis-treatment integrated nanoprobe.

III, Removing a component, which is uncoated effectively, with a dialysis manner in an environment at a pH of 7.4 and the room temperature from the emulsion obtained in the step II to obtain the 19 F-MR/fluorescence multi-mode molecular imaging and drug loading diagnosis-treatment integrated nanoprobe.

Preferably, relative to 5.5 mg of the molecular targeting treatment drug (small-molecule) in the step I, a dosage of the surfactant lecithin 95% (PC) is 45-50 mg, for example, 45 mg, 46 mg, 47 mg, 48 mg, 49 mg or 50 mg.

Preferably, relative to 5.5 mg of the molecular targeting treatment drug (small-molecule) in the step I, a dosage of the cholesterol is 5-6 mg, for example, 5.1 mg, 5.3 mg, 5.4 mg, 5.6 mg, 5.8 mg or 6 mg.

Preferably, relative to 5.5 mg of the molecular targeting treatment drug (small-molecule) in the step I, a dosage of the fluorescent dye is 0-1 mg, for example, 0.1 mg, 0.2 mg, 0.3 mg, 0.5 mg, 0.7 mg, 0.9 mg or 1 mg.

Preferably, relative to 5.5 mg of the molecular targeting treatment drug (small-molecule) in the step I, a dosage of the volatile organic solvent is 100-300 μL, for example, 105 μL, 160 μL, 200 μL, 230 μL, 280 μL or 300 μL.

Preferably, the volatile organic solvent in the step I is chloroform or a mixed solvent of the chloroform and methanol.

Preferably, the stirring in the step I is carried out away from light.

Preferably, the ultrasonic processing in the step I has a frequency of 20-40 kHz, a power of 40-90 W and ultrasonic time of 5-10 min.

A molar ratio of the PFC to the molecular targeting treatment drug (small-molecule) in the step II is (50-1000): 1, for example, 50:1, 70:1, 90:1, 150:1, 200:1, 250:1, 400:1, 600:1, 800:1 or 1000:1, preferably (70-200):1.

Preferably, relative to 5.5 mg of the molecular targeting treatment drug (small-molecule) in the step I, a dosage of the glycerol is 0-0.5 g, for example, 0.1 g, 0.2 g, 0.3 g, 0.4 g or 0.5 g.

Preferably, relative to 5.5 mg of the molecular targeting treatment drug (small-molecule) in the step I, a dosage of the water is 2-5 mL, for example, 2 mL, 2.5 mL, 3 mL, 3.5 mL, 4 mL, 4.5 mL or 5 mL.

Preferably, the water is ultrapure water.

In the present invention, a component that is uncoated effectively is removed with a dialysis manner in an environment at a pH of 7.4 and a room temperature from an emulsion obtained in the step II to obtain the 19 F-MR/fluorescence multi-mode molecular imaging and drug loading diagnosis-treatment integrated nanoprobe.

The present invention provides an application of the above 19 F-MR/fluorescence multi-mode molecular imaging and drug loading diagnosis-treatment integrated nanoprobe in preparing an imaging contrast agent for classification, diagnosis and treatment of a lung cancer.

The present invention has the following beneficial effects: 1, the probe of the present invention may implement in-vivo 19 F-MR molecular imaging and optical imaging as well as accurate diagnosis of a tumor at a molecular level; a carried molecular targeting treatment drug can take a targeted binding effect and can further implement targeted treatment; and by virtue of a characteristic that PFC in a nucleus may carry and release oxygen massively, an anaerobious microenvironment in the tumor is improved, a chemosensitization effect is achieved, and thus the diagnosis-treatment integration of the tumor is implemented finally. 2. An experiment indicates that a 19 F signal enhancement capability of the probe of the present invention is positively correlated with a concentration of a sample; and along with an increase in the concentration of the sample, a signal is enhanced linearly. The probe of the present invention has an excellent 19 F-MRI capability. A drug-loading nanoparticle of the present invention has an excellent targeting anti-tumor effect.

DESCRIPTION OF THE EMBODIMENTS

The present invention is further described below in combination with specific embodiments and FIG. 1 to FIG. 9.

Embodiment 1

Preparation Method of 19 F-MR/Fluorescence Multi-Mode Molecular Imaging and Drug Loading Diagnosis-Treatment Integrated Nanoprobe I. Uniformly mix a molecular targeting treatment drug (small-molecule) with a surfactant and a fluorescent dye, the surfactant coating the molecular targeting treatment drug (small-molecule) physically because of a surface tension; and thereafter, dissolve into a volatile organic solvent, stir for 10 min at a room temperature, evaporate the organic solvent via a rotary evaporator to dryness, then dry for 12 h in a vacuum drying oven at 37° C., and at last, disperse into water via ultrasonic processing to obtain a mixture for later use.

II, Uniformly disperse PFC into the mixture obtained in the step I, add glycerol and the water dropwise, and mix for 5 min in a high-pressure homogenizer to prepare into an emulsion containing the 19 F-MR/fluorescence multi-mode molecular imaging and drug loading diagnosis-treatment integrated nanoprobe.

III, Remove a component, which is uncoated effectively, with a dialysis manner in an environment at a pH of 7.4 and the room temperature from the emulsion obtained in the step II to obtain the 19 F-MR/fluorescence multi-mode molecular imaging and drug loading diagnosis-treatment integrated nanoprobe.

Relative to 5.5 mg of the molecular targeting small-molecule treatment drug in the step I, a dosage of the surfactant lecithin 95% (PC) was 45-50 mg.

Relative to 5.5 mg of the molecular targeting small-molecule treatment drug in the step I, a dosage of the cholesterol was 5-6 mg.

Relative to 5.5 mg of the molecular targeting small-molecule treatment drug in the step I, a dosage of the fluorescent dye was 0-1 mg.

Relative to 5.5 mg of the molecular targeting small-molecule treatment drug in the step 1, a dosage of the volatile organic solvent was 100-300 μL.

The volatile organic solvent in the step I was chloroform or a mixed solvent of the chloroform and methanol.

The stirring in the step I was carried out away from light.

The ultrasonic processing in the step I had a frequency of 20-40 kHz, a power of 40-90 W and ultrasonic time of 5-10 min.

Further, a molar ratio of the PFC to the molecular targeting small-molecule treatment drug in the step II was (70-200): 1.

Relative to 5.5 mg of molecular targeting small-molecule treatment drug in the step 1, a dosage of the glycerol was 0-0.5 g.

Relative to 5.5 mg of molecular targeting small-molecule treatment drug in the step I, a dosage of the water was 2-5 mL.

Or the water was ultrapure water.

Figure 1:
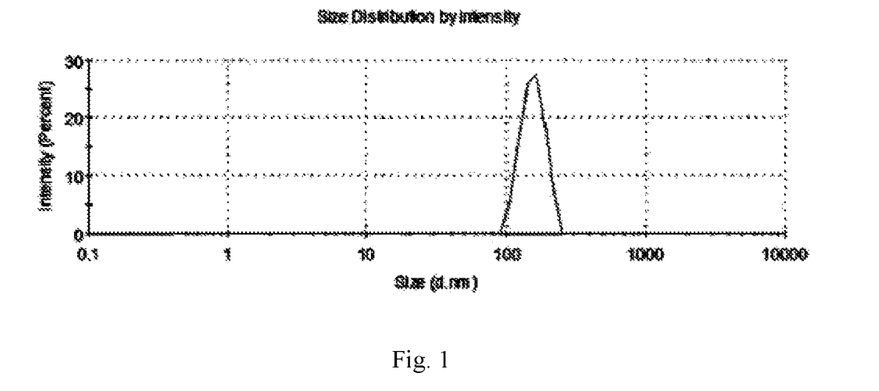
FIG. 1 is a size distribution test of a probe.
Figure 2:
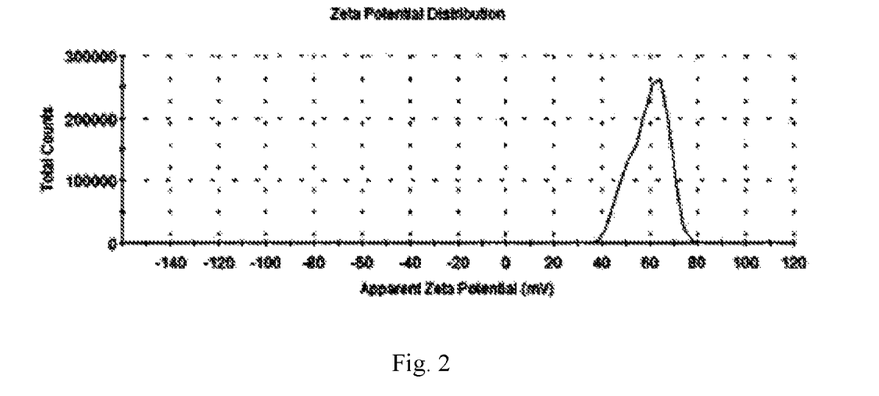
FIG. 2 is an analysis on an apparent zeta potential of a probe.
Figure 3:
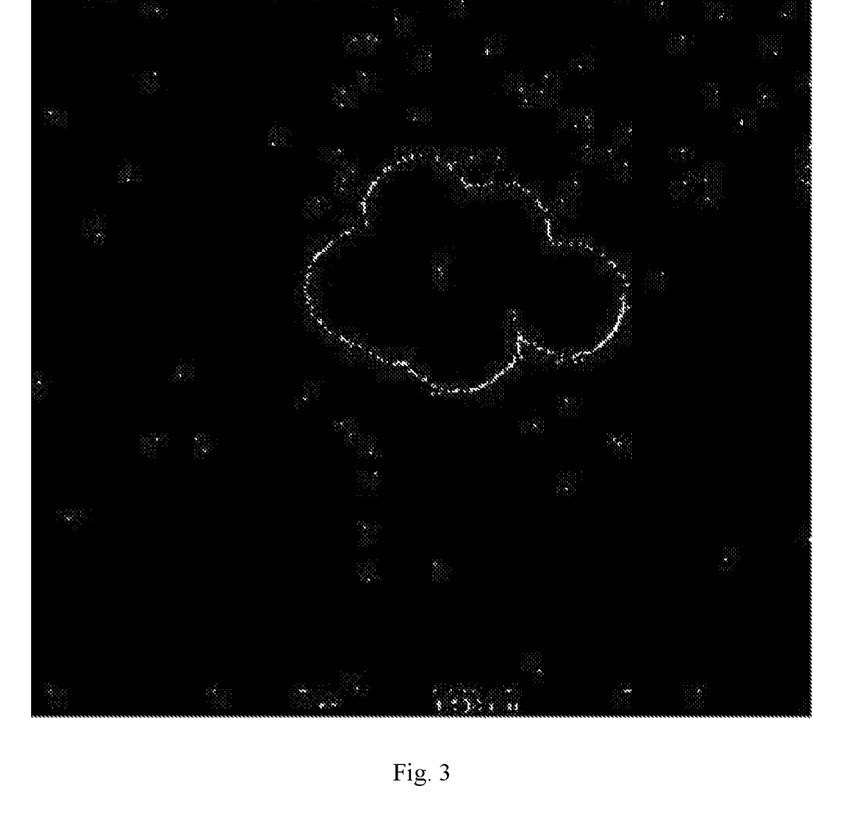
FIG. 3 is a Transmission Electron Microscope (TEM) photo of a probe.

By observing the nanoparticle in Embodiment 1 with a TEM, it is found that the prepared drug-loading nanoparticle is of a spherical structure with a uniform and stable size and has an average particle size of about 115 nm (FIG. 3). With dynamic light scattering for measurement, the size distribution is within 110-130 nm (FIG. 1), which complies with the result observed by the TEM; and the apparent zeta potential is about +62 mV (FIG. 2).

Embodiment 2

Figure 4:
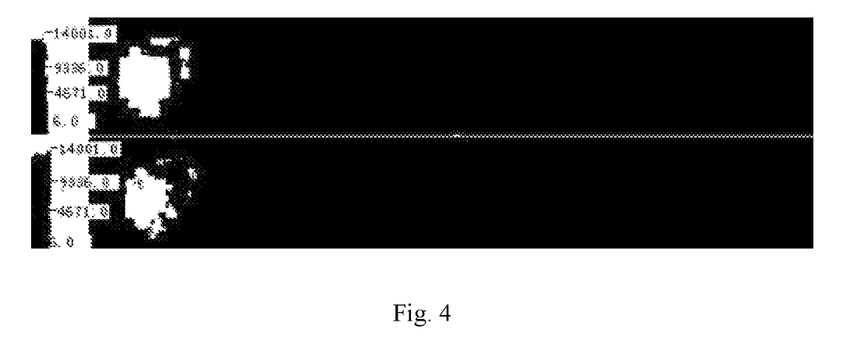
FIG. 4 is a 19 F-MRI phantom image of a probe.

Application of 19 F-MR/Fluorescence Multi-Mode Molecular Imaging and Drug Loading Diagnosis-Treatment Integrated Nanoprobe (Prepared in Embodiment 1) in Taking as Imaging Contrast Agent 1. During 19F-MRI phantom test of the probe, the nanoprobe solution prepared in Embodiment 1 was mixed with a 1.7% Agrose sol to prepare into a phantom sample respectively having a final concentration of 7.67 mmol/L, 15.35 mmol/L, 30.69 mmol/L, 61.38 mmol/L and 122.76 mmol/L; and a 19 F imaging capability was tested, with a result shown in FIG. 4. As can be seen from the result, the 19 F signal enhancement capability of the probe is positively correlated with the concentration of the sample; and along with an increase in the concentration of the sample, a signal is enhanced linearly.

2. MRI after the probe is delivered intravenously

First of all, a naked mouse was anesthetized by isoflurane; and upon successful anesthetization, three naked mice were taken successively, delivered with 300 μL of the probe intravenously according to a numbering sequence, and fixed in a 1H/19 F double-tuned body coil, where a body of each naked mouse was parallel to a scanning bed, a head entered first and a head end was consistent with a direction of a main magnetic field, so that a subcutaneous transplantation tumor was located within a same horizontal line of the center of the 1H119 F body coil. During scanning, a life monitoring system was used to monitor a respiratory rate, and an oxygen supply and a body temperature of 37±0.5° C. for the experimental animal were maintained. The 1H19 F double-tuned body coil was used; a T1W RARE sequence was used for anatomical localization imaging, with an imaging parameter TR=820 ms, TE=12 ms, NA=4, RARE factor=8, matrix=256*256, FOV=38.4*38.4 mm2, and slice thickness=1.5 mm. A 19F RARE sequence was co-localized with 1H, with an imaging parameter TR=2000 ms, TE=10 ms, NA=128, RARE factor=32, matrix=64*64, FOV=38.4*38.4 mm2, and slice thickness=3 mm. The total scanning time was 12 min.

Figure 5:
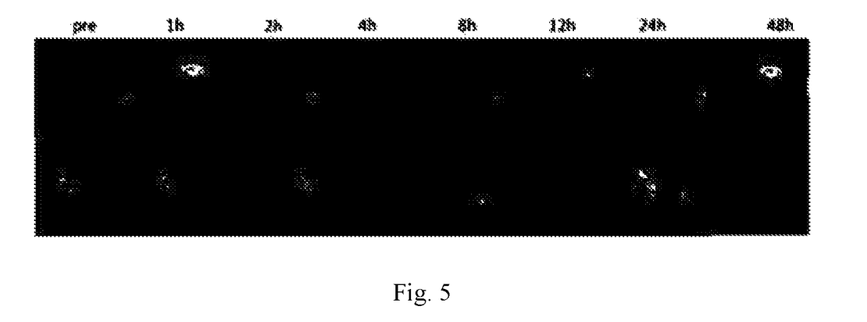
FIG. 5 is a multinuclear MRI image after a probe is delivered intravenously to an H1975 tumor-bearing mouse with lung adenocarcinoma.

After the probe was delivered to the body of the healthy naked mouse intravenously, an MR multinuclear fused image was shown in FIG. 5, with a highlight in the tumor being a multinuclear imaging signal after the probe of the present invention was delivered intravenously. As can be seen from the figure, the probe of the present invention has an excellent 19 F-MRI capability.

Embodiment 3

Evaluation on Efficacy of Probe (Prepared in Embodiment 1) in Targeted Treatment 1. Evaluation on Efficacy of Probe (Prepared in Embodiment 1) at Cell Level A cell was prepared into a single cell suspension by using a culture solution containing 10% of fetal calf serum, and as per 200 μL cells for each pore, the single cell suspension was inoculated to a 96-pore plate, with 200 μL for each pore. Upon overnight incubation, the nanoprobe having different concentrations was added. After 24 h, an MTT solution and DMSO were added, and a mixed solution was placed onto a shaker and vibrated for 15 min at a low speed. A light absorption value of each pore was measured at OD570 nm by using an eliasa.

Figure 6:
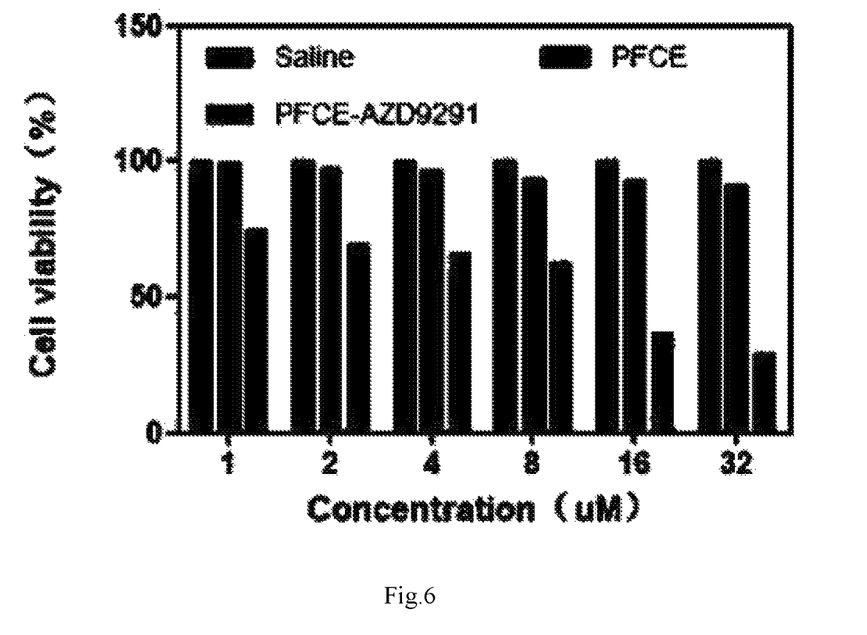
FIG. 6 shows a measurement of a cell vitality after different nanoprobes are used to incubate an H1975 cell for 24 h.

As can be seen from FIG. 6, with the incubation of PFCE, all cells have a viability of greater than 90%, which indicates that the PFCE does not produce a significant cytotoxicity to an H1975 cell. The PFCE-AZD9291 has a higher level of cytotoxicity than the PFCE and saline at 24 h. The PFCE-AZD9291 shows obvious concentration reliance for an in-vitro anti-tumor activity of the H1975 cell.

2. Evaluation on Efficacy of Probe (Prepared in Embodiment 1) in Targeted Treatment of Transplantation Tumor of H1975 Tumor-Bearing Mouse with Lung Adenocarcinoma An H1975 cell at 10 6 was inoculated to a right leg of a Balb/c female naked mouse that was 5-6 weeks old, thus establishing a transplantation tumor. Upon the inoculation of 20 days, when the transplantation tumor was grown to 6-8 mm, a follow-up experiment was carried out. All mice were divided into three groups (n=5), and the mouse in each group was respectively given with the saline, the PFCE and the PFCE-AZD9291. The drug was administered at 50 μL/time every three days. A digital caliper was used to measure a size of the tumor every two days, and a volume was calculated via a formula (L×W2)/2, where the L was a longest diameter of the tumor, and the W was a shortest diameter. Meanwhile, an electronic scale was used to weigh a weight of the mouse. After monitoring of 24 d, the mouse was killed, and the tumor was taken out for histological and immunohistochenmical experiments. A Hematoxylin-Eosin staining (HE staining) tissue slice was used to identify a histopathological change. In order to evaluate proliferation and apoptosis of a tumor cell, proliferating cell nuclear antigen (Ki67) staining and terminal deoxynucleotidyl transferase (TdT) dUTP nick end labeling (TUNEL) staining were carried out.

Figure 7:
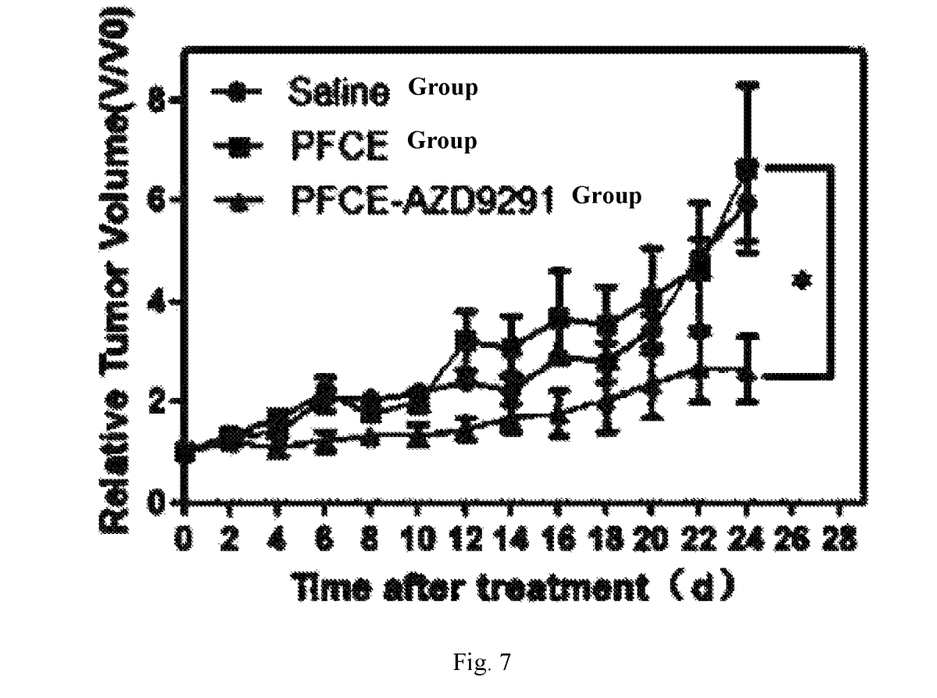
FIG. 7 shows a change of a weight within 24 d when different nanoprobes are used to treat a transplantation tumor of an H1975 tumor-bearing mouse with lung adenocarcinoma.
Figure 8:
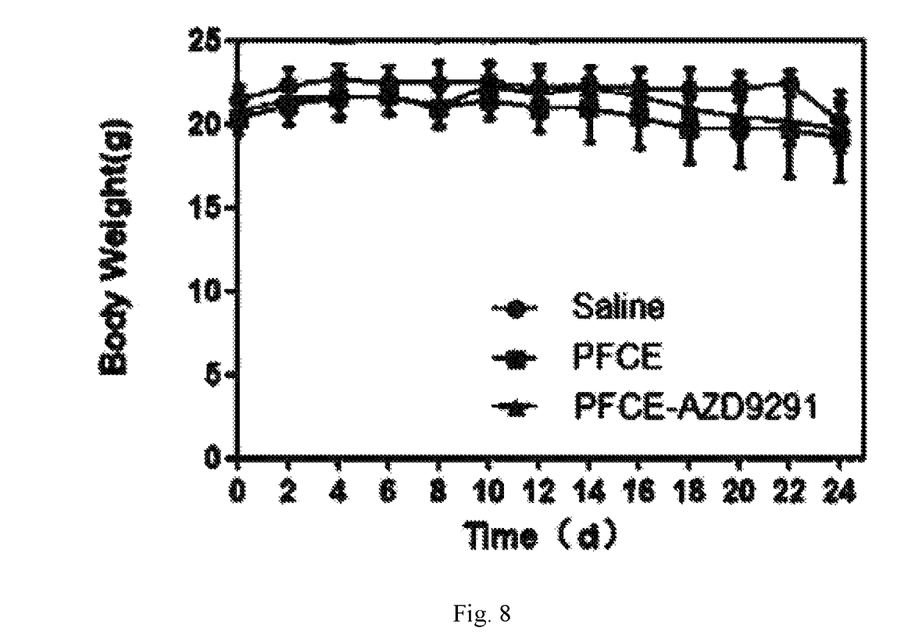
FIG. 8 shows a change of a relative tumor volume within 24 d when different nanoprobes are used to treat a transplantation tumor of an H1975 tumor-bearing mouse with lung adenocarcinoma.
Figure 9:
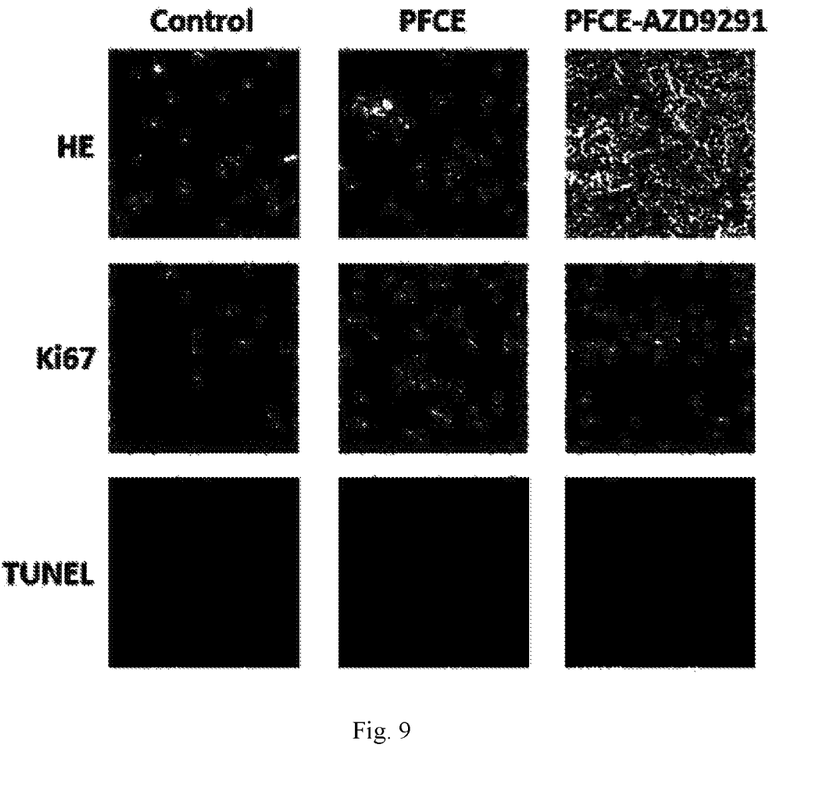
FIG. 9 shows a tumor histological measurement when different nanoprobes are used to treat a transplantation tumor of an H1975 tumor-bearing mouse with lung adenocarcinoma for evaluation of an anti-tumor efficacy.

With analysis on a tumor growth curve, it may be seen that after the tumor of the mouse is treated by the PFCE-AZD9291 nanoparticle, the volume increase is lower than the other two groups, which indicates that the designed nanoparticle loaded with a chemotherapeutic drug has a good anti-tumor effect (FIG. 7). Additionally, there is no statistically significant difference in weight among all groups during treatment (FIG. 8). Furthermore, the HE staining of the tumor slice shows that the number of necrocytosis in the PFCE-AZD9291 group is greater than that in the other two groups, the TUNEL staining shows that the PFCE-AZD9291 group has a great number of apoptotic cells (green fluorescence), and the proliferating cell nuclear antigen (Ki67) staining shows that the number of proliferated cells in the PFCE-AZD9291 group is obviously smaller than that in the saline group and the PFCE group, all of which indicate that the drug-loading nanoparticle of the present invention has the excellent targeting anti-tumor effect (FIG. 9).

What is claimed is:

1. A diagnosis-treatment integrated nano-probe for $^{19}$F-MR/fluorescence multi-mode molecular imaging and drug-loading, wherein the nanoprobe consists of a core, a core shell that surrounds the core, glycerol, and water, the core is a mixture of a surfactant containing a molecular targeting small-molecule treatment drug and fluorescent dye, and the core shell is Perfluorocarbon (PFC) carrier, wherein the molecular targeting small-molecule treatment drug is a third-generation Epidermal Growth Factor Receptor Tyrosine Kinase Inhibitor (EGFR-TKI) AZD9291, and can target a T790M tumor.

2. The diagnosis-treatment integrated nano-probe for $^{19}$F-MR/fluorescence multi-mode molecular imaging and drug-loading according to claim 1, wherein the fluorescent dye is 2-dipalmitoyl-sn-glycero-3-phosphoethanolamine-N-(lissamine rhodamine B sulfonyl)(ammonium salt) (16:0 LissRhod PE) having a wavelength of 580 nm.

3. The diagnosis-treatment integrated nano-probe for $^{19}$F-MR/fluorescence multi-mode molecular imaging and drug-loading according to claim 1, wherein the PFC is Perfluoro-15-Crown-5-Ether (PFCE).

4. A preparation method of the diagnosis-treatment integrated nano-probe for $^{19}$F-MR/fluorescence multi-mode molecular imaging and drug-loading according to claim 1, comprising the following steps: obtaining a mixture of a surfactant containing a molecular targeting small-molecule treatment drug and a fluorescent dye, and using Perfluorocarbon (PFC) as a carrier to coat the mixture to form a nanoparticle;

and uniformly mixing the nanoparticle with glycerol and water to obtain the 19F-MR/fluorescence multi-mode molecular imaging and drug loading diagnosis-treatment integrated nanoprobe.

5. The preparation method according to claim 4, comprising the following steps I-III:

I, uniformly mixing a molecular targeting small-molecule treatment drug with a surfactant and a fluorescent dye to get a pre-mixed mixture, wherein, the surfactant coating the molecular targeting small-molecule treatment drug physically because of a surface tension; and dissolving the pre-mixed mixture into a volatile organic solvent, stirring for 10 min at a room temperature, evaporating the volatile organic solvent via a rotary evaporator to dryness, then drying for 12 h in a vacuum drying oven at 37° C., and at last, dispersing into water via ultrasonic processing to obtain a mixture for later use;

II, uniformly dispersing PFC into the mixture obtained in the step I, adding glycerol and the water dropwise, and mixing for 5 min in a high-pressure homogenizer to prepare into an emulsion containing the 19 F-MR/fluorescence multi-mode molecular imaging and drug loading diagnosis-treatment integrated nanoprobe; and III, removing a component, which is uncoated effectively, with a dialysis manner in an environment at a pH of 7.4 and the room temperature from the emulsion obtained in the step II to obtain the 19 F-MR/fluorescence multi-mode molecular imaging and drug loading diagnosis-treatment integrated nanoprobe.

6. The preparation method according to claim 5, wherein the surfactant is lecithin 95% and cholesterol, and taking 5.5 mg of the molecular targeting small-molecule treatment drug in the step I as a standard to weight dosages of the surfactant, the fluorescent dye and the volatile organic solvent, and relative to 5.5 mg of the molecular targeting small-molecule treatment drug in the step I, a dosage of the surfactant lecithin 95% is 45-50 mg; relative to 5.5 mg of the molecular targeting small-molecule treatment drug in the step I, a dosage of the surfactant cholesterol is 5-6 mg; relative to 5.5 mg of the molecular targeting small-molecule treatment drug in the step I, a dosage of the fluorescent dye is 0.1-1 mg; relative to 5.5 mg of the molecular targeting small-molecule treatment drug in the step I, a dosage of the volatile organic solvent is 100-300 μL; the volatile organic solvent in the step I is chloroform or a mixed solvent of the chloroform and methanol; the stirring in the step I is carried out away from light; and the ultrasonic processing in the step I has a frequency of 20-40 kHz, a power of 40-90 W and ultrasonic time of 5-10 min.

7. The preparation method according to claim 6, wherein a molar ratio of the PFC to the molecular targeting small-molecule treatment drug in the step II is 50-1000:1; relative to 5.5 mg of molecular targeting small-molecule treatment drug in the step I, a dosage of the glycerol is 0.1-0.5 g; and relative to 5.5 mg of molecular targeting small-molecule treatment drug in the step I, a dosage of the water is 2-5 mL.

\* \* \* \* \*